United States Patent
Kim et al.

(10) Patent No.: US 9,383,372 B2
(45) Date of Patent: Jul. 5, 2016

(54) DISK-TYPE MICROFLUIDIC SYSTEM AND METHOD FOR MEASURING DEFORMABILITY OF BLOOD CELLS

(71) Applicant: POSTECH ACADEMY-INDUSTRY FOUNDATION, Pohang-si (KR)

(72) Inventors: Dong Sung Kim, Pohang-si (KR); Moonwoo La, Chuncheon-si (KR)

(73) Assignee: POSTECH ACADEMY-INDUSTRY FOUNDATION, Pohang-Si (KR)

( * ) Notice: Subject to any disclaimer, the term of this patent is extended or adjusted under 35 U.S.C. 154(b) by 72 days.

(21) Appl. No.: 14/360,675

(22) PCT Filed: Dec. 12, 2012

(86) PCT No.: PCT/KR2012/010796
§ 371 (c)(1),
(2) Date: May 27, 2014

(87) PCT Pub. No.: WO2013/089432
PCT Pub. Date: Jun. 20, 2013

(65) Prior Publication Data
US 2014/0342391 A1 Nov. 20, 2014

(30) Foreign Application Priority Data
Dec. 12, 2011 (KR) ........................ 10-2011-0133259

(51) Int. Cl.
*G01N 35/00* (2006.01)
*G01N 33/80* (2006.01)
*G01N 33/49* (2006.01)
*G01N 21/07* (2006.01)
*G01N 35/04* (2006.01)

(52) U.S. Cl.
CPC .............. *G01N 33/80* (2013.01); *G01N 33/491* (2013.01); *G01N 35/00069* (2013.01); *G01N 21/07* (2013.01); *G01N 2035/0449* (2013.01)

(58) Field of Classification Search
None
See application file for complete search history.

(56) References Cited

U.S. PATENT DOCUMENTS
2001/0022654 A1   9/2001  Kensey

FOREIGN PATENT DOCUMENTS
CN   1806171    7/2006
EP   1063515   12/2000
EP   2028496    2/2009

(Continued)

OTHER PUBLICATIONS

Hoffman, J.F. et al. Directly observed reversible shape changes and hemoglobin stratification during centrifugation of human and Amphiuma red blood cells, 2006, PNAS, vol. 103(8), pp. 2971-2976.*

(Continued)

*Primary Examiner* — Robert Xu
(74) *Attorney, Agent, or Firm* — Lex IP Meister, PLLC (57) ABSTRACT

A method for measuring a degree of deformation of blood cells includes: supplying blood to a centrifugal container of a disk; centrifuging the blood in the centrifugal container to blood cells and plasma by rotating the disk and detecting an actual moving distance of the blood cells in the centrifugal container every hour; and calculating a first curve representing the actual moving distance of the blood cells in the centrifugal container every hour and a second curve representing a theoretical moving distance of the blood cells every hour and measuring a degree of deformation of the blood cells by comparing the first curve and the second curve.

2 Claims, 6 Drawing Sheets

(56) References Cited

FOREIGN PATENT DOCUMENTS

| | | |
|---|---|---|
| JP | 2002-503331 | 1/2002 |
| JP | 2007-521478 | 8/2007 |
| KR | 10-2005-0000312 | 1/2005 |
| KR | 10-0915195 | 8/2009 |
| KR | 10-2010-0101526 | 9/2010 |
| WO | 96/39618 | 12/1996 |
| WO | 2004/113908 | 12/2004 |
| WO | 2008/021626 | 2/2008 |
| WO | 2009/091186 | 7/2009 |
| WO | 2010-104292 | 9/2010 |

OTHER PUBLICATIONS

Chinese Patent Office, Chinese Search Report dated Jan. 16, 2015, which was attached to the Office Action dated Jan. 27, 2015, of the corresponding Chinese Patent Application No. 201280061012.4.

* cited by examiner

DISK-TYPE MICROFLUIDIC SYSTEM AND METHOD FOR MEASURING DEFORMABILITY OF BLOOD CELLS

TECHNICAL FIELD

The present invention relates to a disk-shaped microfluidic system and a method for measuring a degree of deformation of blood cells.

BACKGROUND ART

Generally, blood separation, plasma extraction, property analysis of blood, and the like are performed by equipment or apparatuses suitable for the respective purposes. The blood is divided into the plasma and blood cells by an apparatus such as a centrifuge, and the divided plasma is extracted by pipetting and the like. Further, properties of the blood such as viscosity, hematocrit, and the like of the blood may be analyzed by dedicated equipment for measuring each property.

A series of processes through the dedicated equipment have an advantage of more accurately performing each process, but there are disadvantages that in order to check the blood condition, a large amount of blood may be used, and a long testing time for checking all blood conditions is taken due to non-continuous processes.

The above information disclosed in this Background section is only for enhancement of understanding of the background of the invention and therefore it may contain information that does not form the prior art that is already known in this country to a person of ordinary skill in the art.

DISCLOSURE

Technical Problem

The present invention has been made in an effort to provide a disk-shaped microfluidic system, and a method for measuring a degree of deformation of blood cells, having advantages of extracting plasma by centrifuging blood and simultaneously checking a blood condition.

Technical Solution

A first aspect of the present invention provides a method for measuring a degree of deformation of blood cells. The method includes: supplying blood to a centrifugal container of a disk; centrifuging the blood in the centrifugal container to blood cells and plasma by rotating the disk and detecting an actual moving distance of the blood cells in the centrifugal container every hour; and calculating a first curve representing the actual moving distance of the blood cells in the centrifugal container every hour and a second curve representing a theoretical moving distance of the blood cells every hour and measuring a degree of deformation of the blood cells by comparing the first curve and the second curve.

The detecting of the actual moving distance of the blood cells may use an image acquired by photographing the inside of the centrifugal container every hour.

The detecting of the actual moving distance of the blood cells may be performed by calculating a center of mass with respect to a dark area by analyzing contrast in the image and measuring a short distance of the dark area based on the center of mass.

The measuring of the degree of deformation of the blood cells may be performed by calculating the second curve by using the following equation and using at least one of a height difference between the first curve and the second curve and a slope difference between the first curve and the second curve.

$$\frac{\pi}{6} p_p d_p^3 r_p'' = \frac{\pi}{6}(p_p - p_f)d_p^3 w^2 r_p - 3\pi d_p r_p' \left\{ u_f(1+\theta^{1/3}) \exp\left[\frac{5\theta}{3(1-\theta)}\right] \right\}$$

In the equation, $\pi$ is a circle constant, $p_p$ is the density of the blood, $d_p$ is a diameter of the blood cells, $r''_p$ is a moving acceleration of the blood cells, $p_f$ is the density of the plasma, $w$ is an angular velocity of the disk, $r_p$ is a moving distance of the blood cells, $r'_p$ is a moving speed of the blood cells, $u_f$ is the viscosity of the plasma, and $\theta$ is a volume ratio of the blood cells to the entire volume of the blood.

A second aspect of the present invention provides a disk-shaped microfluidic system including: a disk including a centrifugal container to which blood is supplied and centrifuging the blood in the centrifugal container to blood cells and plasma; a photographing unit positioned at the upper side of the disk and photographing inside of the centrifugal container every hour; and a controller connected with the photographing unit, detecting an actual moving distance of the blood cells in the centrifugal container every hour by using the image photographed by the photographing unit, detecting and displaying a first curve representing the actual moving distance of the blood cells in the centrifugal container every hour and a second curve representing a theoretical moving distance of the blood cells every hour, and measuring a degree of deformation of the blood cells by comparing the first curve and the second curve.

The controller may calculate the second curve using the following equation and measure the degree of deformation of the blood cells by using at least one of a height difference between the first curve and the second curve and a slope difference between the first curve and the second curve.

$$\frac{\pi}{6} p_p d_p^3 r_p'' = \frac{\pi}{6}(p_p - p_f)d_p^3 w^2 r_p - 3\pi d_p r_p' \left\{ u_f(1+\theta^{1/3}) \exp\left[\frac{5\theta}{3(1-\theta)}\right] \right\}$$

In the equation, $\pi$ is a circle constant, $p_p$ is the density of the blood, $d_p$ is a diameter of the blood cells, $r''_p$ is a moving acceleration of the blood cells, $p_f$ is the density of the plasma, $w$ is an angular velocity of the disk, $r_p$ is a moving distance of the blood cells, $r'_p$ is a moving speed of the blood cells, $u_f$ is the viscosity of the plasma, and $\theta$ is a volume ratio of the blood cells to the entire volume of the blood.

The disk may further include a plasma container connected with the centrifugal container, and a micro-valve connected between the centrifugal container and the plasma container. According to the exemplary embodiment of the present invention, it is possible to provide a disk-shaped microfluidic system and a method for measuring a degree of blood cells that extract plasma by centrifuging blood, and simultaneously checking a blood condition.

MODE FOR INVENTION

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

The drawings and description are to be regarded as illustrative in nature and not restrictive. Like reference numerals designate like elements throughout the specification.

Further, the size and thickness of each configuration shown in the drawings are arbitrarily shown for better understanding and ease of description, but the present invention is not limited thereto.

In the drawings, for better understanding and ease of description, the thickness of some layers and areas is exaggerated. It will be understood that when an element such as a layer, film, region, or substrate is referred to as being "on" another element, it can be directly on the other element or intervening elements may also be present.

In addition, unless explicitly described to the contrary, the word "comprise" and variations such as "comprises" or "comprising" will be understood to imply the inclusion of stated elements but not the exclusion of any other elements. Further, in the specification, the word "on" means positioning on or below the object portion, and does not essentially mean positioning on the upper side of the object portion based on a gravity direction.

Hereinafter, a disk-shaped microfluidic system according to a first exemplary embodiment of the present invention will be described with reference to FIG. 1 and FIG. 2.

Figure 1:
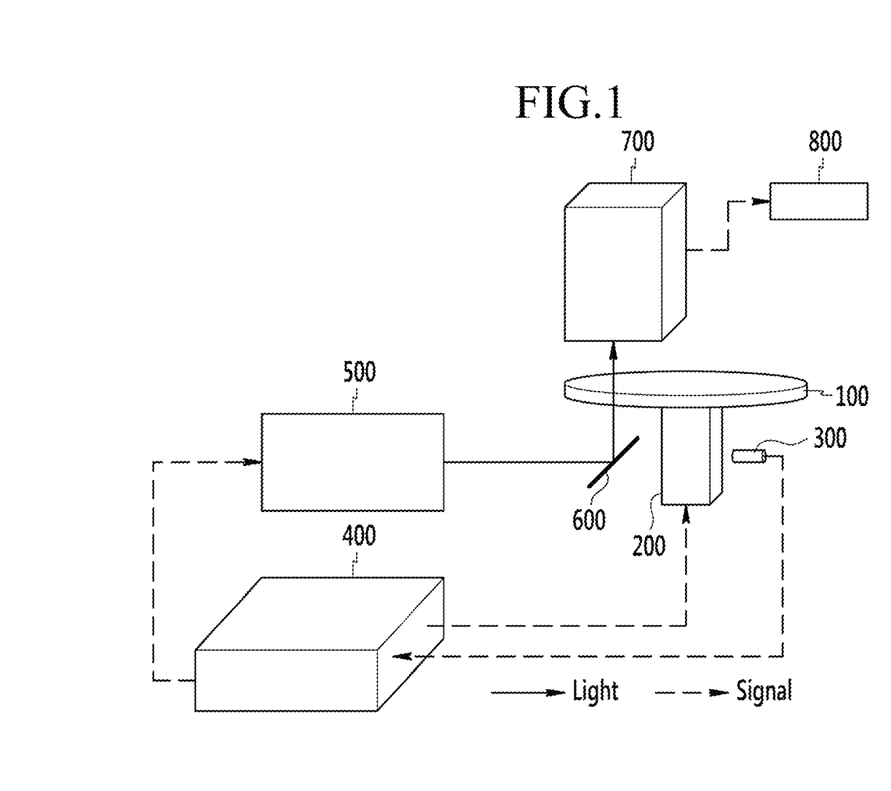
FIG. 1 illustrates a disk-shaped microfluidic system according to a first exemplary embodiment of the present invention.

FIG. 1 illustrates a disk-shaped microfluidic system according to the first exemplary embodiment of the present invention.

As shown in FIG. 1, the disk-shaped microfluidic system according to the first exemplary embodiment of the present invention centrifuges blood and at the same time determines a blood condition, and includes a disk 100, driver 200, a sensor 300, an adjustor 400, an illuminator 500, a mirror 600, a photographing unit 700, and a controller 800.

Figure 2:
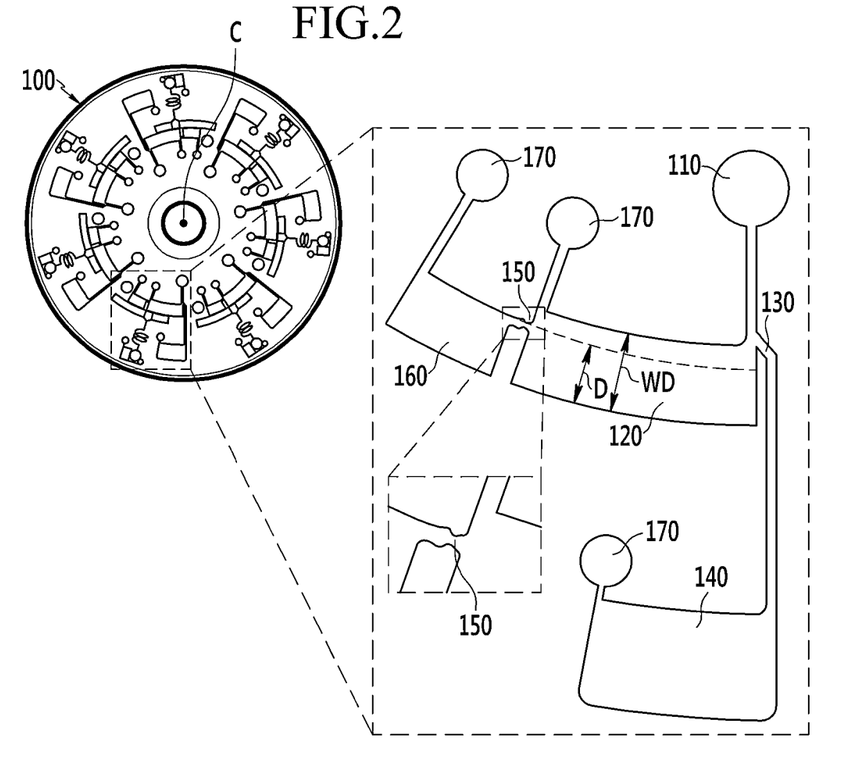
FIG. 2 illustrates a disk shown in FIG. 1.

FIG. 2 illustrates the disk of FIG. 1.

As shown in FIG. 2, the disk 100 is formed in the shape of a round disk, and centrifuges externally supplied blood into blood cells and plasma by rotating itself based on a center axis C. In the disk 100, an injection port 110, a centrifugal container 120, a waste flow channel 130, a waste receiving container 140, a micro-valve 150, a plasma container 160, and an air discharge port 170 may be formed by intaglio through a mass production method, such as injection molding using MEMS technology such as photolithography or insert molding having an opposite shape, hot embossing, UV-molding, and casting. The disk 100 may be made of a metal material, a ceramic material, and a polymer material, such as cyclic olefin copolymer (COC), polymethylmethacrylate (PMMA), polystyrene (PS), polycarbonate (PC), polydimethylsiloxane (PDMS), polytetrafluoroethylene (Teflon), and polyvinylchloride (PVC).

The injection port 110 is adjacent to the central shaft C to be disposed in the disk 100, and is a passage to which blood is supplied.

The centrifugal container 120 is connected with the injection port 110, and is a container in which the blood supplied from the injection port 110 is placed. When the disk 100 rotates, the blood is centrifuged to separate blood cells and plasma in the centrifugal container 120.

The waste flow channel 130 is a passage which is positioned between the centrifugal container 120 and the injection port 110, and through which the blood overflowing from the centrifugal container 120 moves to the waste receiving container 140 while rotating the disk 100.

The waste receiving container 140 is a container which is connected with the centrifugal container 120 by the waste flow channel 130, and receives the blood flowing from the centrifugal container 120 while rotating the disk 100.

The micro-valve 150 is a passage which is connected between the centrifugal container 120 and the plasma container 160, of which a position is determined by considering hematocrit of the blood, and through which only the centrifuged plasma passes in the centrifugal container 120 by determining the position thereof. In more detail, the micro-valve 150 may be disposed to correspond to one width D of 30% to 60% of an entire width WD of the centrifugal container 120 by considering 30% to 60% as a general range of the hematocrit. The micro-valve 150 may adjust opening and closing according to an angular velocity of the disk 100. In detail, the opening and closing of the micro-valve 150 is adjusted due to a difference between a first pressure formed around the micro-valve 150 by centrifugal force according to rotation of the disk 100 and a second pressure formed by surface tension in the micro-valve 150. For example, when the first pressure is larger than the second pressure, the micro-valve 150 opens and then the plasma moves to the plasma container 160 from the centrifugal container 120 through the micro-valve 150, and when the second pressure is larger than the first pressure, the micro-valve 150 closes and then the blood does not move to the plasma container 160 from the centrifugal container 120 through the micro-valve 150. Since the first pressure is proportional to the angular velocity of the disk 100, the second pressure is adjusted to be larger than the first pressure when the blood is centrifuged, and the first pressure is adjusted to be larger than the second pressure when the plasma is extracted by adjusting the angular velocity of the disk 100, and as a result, each of the closing and the opening of the micro-valve 150 may be adjusted in response to each of the centrifugation and the plasma extraction by adjusting the angular velocity of the disk 100.

The plasma container 160 is a container which is connected with the centrifugal container 120 through the micro-valve 150 to receive the plasma centrifuged from the blood in the centrifugal container 120. The plasma received in the plasma container 160 may move to another container through one channel connected with the plasma container 160 to be stored.

The air discharge port 170 is connected to each of the centrifugal container 120, the waste receiving container 140, and the plasma container 160, and a passage through which air occupied in each container is discharged when a fluid such as blood and plasma are supplied to each container.

Hereinafter, centrifugation of blood in the disk of the disk-shaped microfluidic system according to the first exemplary embodiment of the present invention will be described with reference to FIG. 3.

Figure 3:
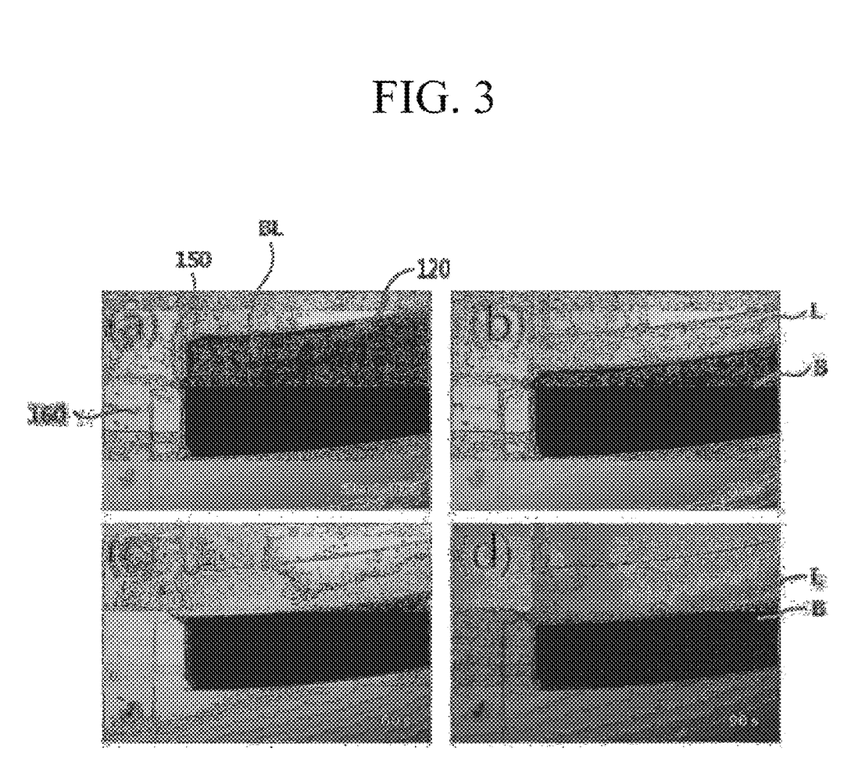
FIG. 3 shows photographs illustrating centrifugation of blood using the disk-shaped microfluidic system according to the first exemplary embodiment of the present invention.

FIG. 3 shows photographs illustrating centrifugation of blood in the disk of the disk-shaped microfluidic system according to the first exemplary embodiment of the present invention.

FIG. 3(a) to (d) are photographs illustrating an experiment process of centrifugation of a small amount of blood performed by using the disk 100 of an actually manufactured disk-shaped microfluidic system with the passage of time. As shown in FIG. 3(*a*) to (*d*), centrifugation of blood BL injected into the centrifugal container 120 by centrifugal force which is caused by rotating the disk 100 is performed. In this process, as illustrated in FIG. 3(*b*), the blood BL is accurately divided into blood cells B and plasma L, and the blood cells B are precipitated in an outer direction of a rotation center, and are no longer precipitated after a predetermined time as illustrated in FIG. 3(*d*). Further, while the centrifugation of the blood BL is performed, the movement of the blood or the plasma is prevented by the micro-valve 150.

Thereafter, the micro-valve 150 is opened by increasing the angular velocity of the disk 100 to induce the extraction of the centrifuged plasma L. The plasma L separated on an upper portion of the centrifugal container 120 moves to the plasma container 160 through the micro-valve 150. As a result, it may be verified that a small amount of blood may be centrifuged and the plasma may be extracted by a convenient and efficient method using the disk 100 of the disk-shaped microfluidic system according to the first exemplary embodiment of the present invention.

Referring back to FIG. 1, the driver 200 supports the disk 100, and includes a driving means of a motor and the like to rotate the disk 100.

The sensor 300 is positioned to be adjacent to the disk 100 and serves to sense the number of revolutions of the disk 100.

The adjustor 400 is connected with the sensor 300 and the driver 200, and serves to receive a signal from the sensor 300 sensing the number of revolutions of the disk 100 to adjust the rotation of the disk 100 by the driver 200. The angular velocity of the disk 100 may be adjusted by the adjustor 400.

The illuminator 500 is connected with the adjustor 400, and reflects light to the mirror 600 in a flash form in synchronization with the number of revolutions of the disk 100.

The mirror 600 is positioned at a lower side of the disk 100, and reflects the light irradiated from the illuminator 500 in a disk 100 direction.

The photographing unit 700 is positioned at the upper side of the disk 100 to correspond to the centrifugal container 120 of the disk 100 and the mirror 600, and photographs an inside of the centrifugal container 120 every hour by using the light in synchronization with the number of revolutions of the disk 100. The photographing unit 700 photographs the inside of the centrifugal container 120 every hour.

The controller 800 is connected with the photographing unit 700, detects an actual moving distance of the blood cells in the centrifugal container 120 every hour by using the image photographed by the photographing unit 700, calculates a first curve showing an actual moving distance of the blood cells every hour and a second curve showing a theoretical moving distance of the blood cells every hour, and calculates hematocrit of the blood and viscosity of the plasma by comparing the first curve and the second curve. That is, the controller 800 checks the blood condition by measuring a degree of deformation of the blood cells centrifuged from the blood in the disk 100.

The controller 800 calculates the second curve using the following equation, and measures a degree of deformation of blood cells using at least one of a height difference between the first curve and the second curve and a slope difference between the first curve and the second curve.

$$\frac{\pi}{6} p_p d_p^3 r_p'' =$$ [Equation]

-continued
$$\frac{\pi}{6}(p_p - p_f)d_p^3 w^2 r_p - 3\pi d_p r_p' \left\{ u_f (1 + \theta^{1/3}) \exp\left[\frac{5\theta}{3(1-\theta)}\right] \right\}$$

In the equation, $\pi$ is a circle constant, $p_p$ is the density of the blood, $d_p$ is a diameter of the blood cells, $r''_p$ is a moving acceleration of the blood cells, $p_f$ is the density of the plasma, $w$ is an angular velocity of the disk, $r_p$ is a moving distance of the blood cells, $r'_p$ is a moving speed of the blood cells, $u_f$ is the viscosity of the plasma, and $\theta$ is a volume ratio of the blood cells to the entire volume the blood.

Hereinafter, a method for measuring a degree of deformation of blood cells according to a second exemplary embodiment of the present invention using the disk-shaped microfluidic system according to the first exemplary embodiment of the present invention described above will be described with reference to FIG. 4 to FIG. 6.

Figure 4:
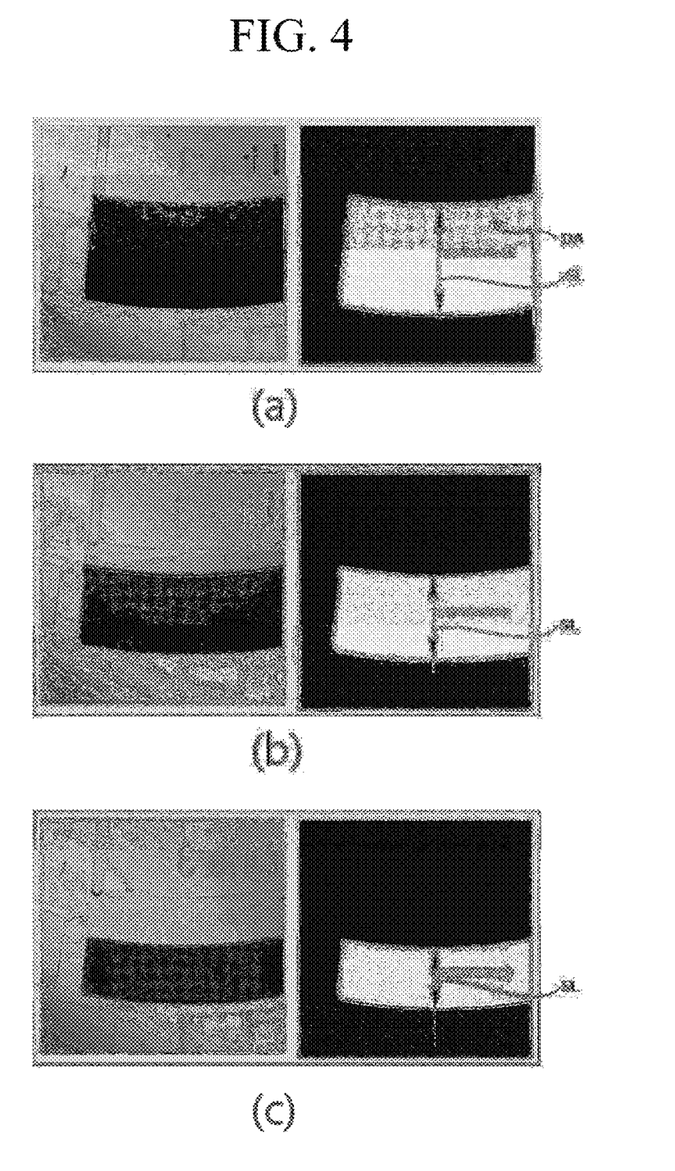
FIG. 4 to FIG. 6 are provided for description of a method for measuring a degree of deformation of blood cells according to a second exemplary embodiment of the present invention.
Figure 5:
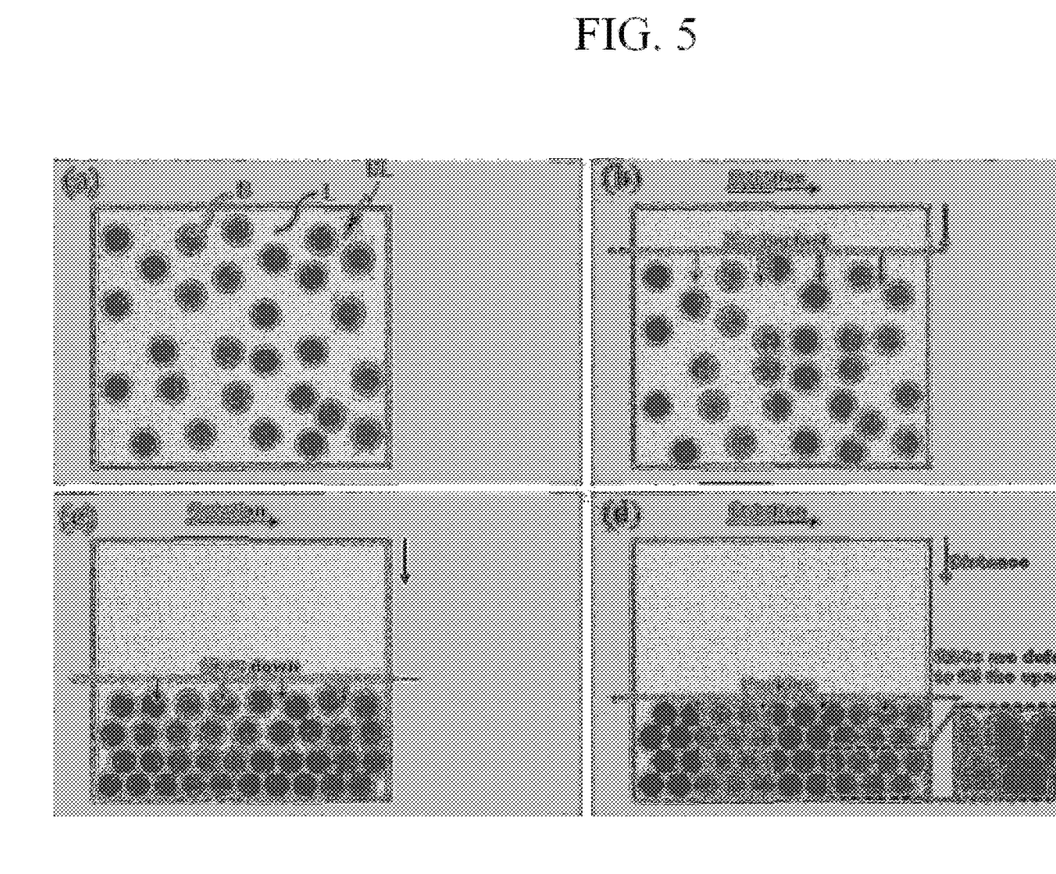
Figure 6:
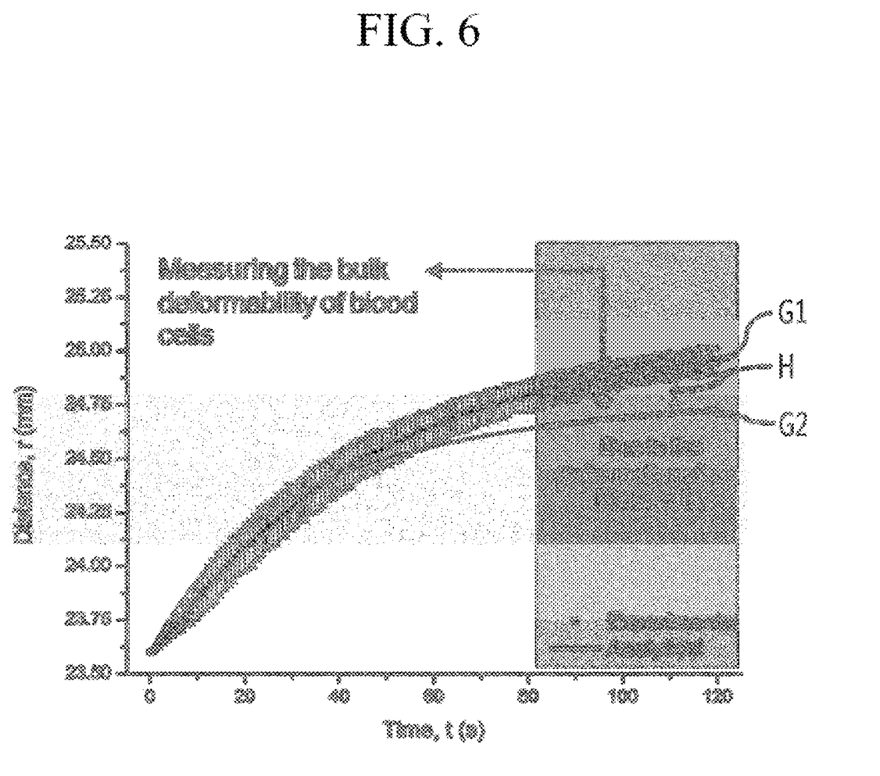

FIG. 4 to FIG. 6 are diagrams for description of a method for measuring a degree of deformation of blood cells according to the second exemplary embodiment of the present invention.

First, the blood is supplied to the centrifugal container 120 of the disk 100.

Next, the blood in the centrifugal container 120 is centrifuged into blood cells and plasma by rotating the disk 100, and an actual moving distance of the blood cells in the centrifugal container 120 is detected every hour.

FIG. 4 shows photographs illustrating an image of the inside of the centrifugal container every hour.

In detail, as shown in FIG. 4, original photographs (left image of each of (a), (b), and (c)) of the inside of the centrifugal container 120 every hour are corrected to post-images (right image of each of (a), (b), and (c)) by analyzing contrast. In this case, in the post-image, the precipitation of the blood cells is changed to white, and the background is changed to black. Thereafter, a center of mass of a dark area (DA) which is the precipitation of the blood cells of the post-image is calculated, and a short distance (SL) of the dark area (DA) is measured based on the center of mass to detect the actual moving distance of the blood cells in the centrifugal container 120 every hour. Such a process is performed with respect to the entire image frame, and as a result, data showing a precipitated height of the blood cells with time may be obtained. The detection may be performed by the controller 800.

Next, a degree of deformation of the blood cells is measured.

In detail, the first curve showing the actual moving distance of the blood cells every hour and the second curve showing the theoretical moving distance of the blood cells every hour are calculated, and the degree of deformation of the blood cells is measured by comparing the first curve and the second curve.

Hereinafter, the method for measuring the degree of deformation of the blood cells will be described in further detail.

FIG. 5 illustrates deformation of the blood cells in the centrifugation process of blood.

FIG. 5(*a*) illustrates blood cells B that are evenly spread in the plasma L in the blood BL. The amount of materials existing in the blood BL, excluding the blood cells B, is small enough to be negligible, or the size of the material is very small and thus it is permissible for it to be considered as a part of the plasma L.

FIG. 5(*a*) to (*d*) illustrate precipitation of the blood cells B when a centrifugal force is generated due to rotation of the disk in the disk-shaped microfluidic system. As shown in FIG. 5(*b*), unit cells of blood cells B are far from each other at an initial stage and thus precipitation speed of the blood cells B becomes fast. When a predetermined time elapses, the unit cells of the blood cells B become close to each other as shown in FIG. 5(c), and thus the precipitation speed is slowed. After the unit cells of the blood cells B are completely arranged in the bottom surface, the unit cells of the blood cells B are deformed and thus fill the gaps between every neighboring blood cells B such that the height of the precipitation layer is slowly lowered. That is, the method for measuring the degree of deformation of the blood cells according to the secondary exemplary embodiment of the present invention measures the degree of deformation of the blood cells based on that fact that the decrease speed of the height of the precipitation layer is closely related to the degree of deformation of the blood cells.

FIG. 6 is a graph illustrating a first curve that shows actual moving distance of the blood cells every hour and a second curve that shows a theoretical moving distance of the blood cells every hour. In FIG. 6, the x-axis represents time (second) and the y-axis represents moving distance (mm) of the blood cells.

As illustrated in FIG. 5, a first curve G1 which is an experimental graph showing the actual moving distance of the blood cells every hour is detected by analyzing the image obtained through the photographing unit 700 of the disk-shaped microfluidic system, as described above.

A second curve G2 which is a theoretical graph showing the theoretical moving distance of the blood cells every hour is calculated by the following equation.

$$\frac{\pi}{6} p_p d_p^3 r_p'' = $$ [Equation]
$$\frac{\pi}{6}(p_p - p_f)d_p^3 w^2 r_p - 3\pi d_p r_p' \left\{ u_f(1+\theta^{1/3})\exp\left[\frac{5\theta}{3(1-\theta)}\right]\right\}$$

In the equation, $\pi$ is a circle constant, $p_p$ is the density of the blood, $d_p$ is a diameter of the blood cells, $r_p''$ is a moving acceleration of the blood cells, pf is the density of the plasma, w is an angular velocity of the disk, $r_p$ is a moving distance of the blood cells, $r_p'$ is a moving speed of the blood cells, $u_f$ is the viscosity of the plasma, and $\theta$ is a volume ratio of the blood cells to the entire volume of the blood.

The equation is configured based on a dynamic force balance formed by a plurality of globular particles, when the globular particles existing in a specific fluid are precipitated by centrifugal force. First, when one globular particle is precipitated by centrifugal force in the specific fluid, movement of the particle forms a dynamic force balance by centrifugal force, buoyancy force, and drag force, and when the blood cell is assumed to be a rigid body, that is, a particle without deformation, a viscosity value of the fluid including a plurality of particles instead of the viscosity of the fluid is applied by considering a condition where the plurality of particles are precipitated, and as a result, the equation is derived by mathematizing the condition.

Iterations are performed based on the equation to calculate the second curve G2. When the second curve G2 is calculated, $r_p''$, $r_p'$, and $r_p$ are calculated by applying predetermined theoretical values to $\pi$, $p_p$, $d_p$, $p_f$, w, $u_f$, and $\theta$.

The degree of deformation of the blood cells is measured by comparing the first curve G1 and the second curve G2.

In the second curve G2, which is a theoretical graph, the blood cell is assumed to be a rigid body, and thus it can be observed that no further precipitation is performed after a predetermined time has elapsed. This is because, after the blood cell particles are aligned in the bottom surface, the blood cells do not fill the gaps due to the characteristic of the rigid body so that the blood cells can maintain a constant distance without further precipitation. On the other hand, it can be observed in the first curve G1, which is an actual graph, that precipitation is continuously performed in the actual blood cells even after a constant time elapsed. This is also caused due to the degree of deformation of the blood cells. Therefore, a difference between the first curve G1 and the second curve G1 indicates the degree of deformation of the blood cells.

That is, the method for measuring the degree of deformation of the blood cells according to the second exemplary embodiment of the present invention measures the degree of deformation of the blood cells using at least one of a difference of height H (i.e., moving distance difference of the blood cells, which is the y-axis) between the first curve G1 and the second curve G2 and a slope difference between the first curve G1 and the second curve G2. Here, the height difference is a difference of the precipitation height between the second curve G2, which is a theoretical graph, and the first curve G1, which is the experimental graph, and the slope difference is a difference of precipitation speed (i.e., moving speed difference of blood cells).

As such, by comparing the first curve G1 which is the experimental graph showing a development of the blood centrifugation and the second curve G2 which is the theoretical graph, the degree of deformation of blood cells which are important properties of the blood may be measured, and the measured degree of deformation of the blood cells may be used as a criterion for estimating the blood condition.

As described above, by the disk-shaped microfluidic system according to the first exemplary embodiment of the present invention and the method for measuring the degree of deformation of blood cells according to the second exemplary embodiment of the present invention, the blood is centrifuged to extract the plasma, and simultaneously the blood condition is checked, and as a result, additional equipment for checking the blood condition is not required, and simultaneously, additional time for checking the blood condition is not required.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A disk-shaped microfluidic system comprising:
    a disk including a centrifugal container to which blood is supplied and centrifuging the blood in the centrifugal container to blood cells and plasma;
    a photographing unit positioned at the upper side of the disk and photographing inside of the centrifugal container every hour; and
    a controller connected with the photographing unit, detecting an actual moving distance of the blood cells in the centrifugal container every hour by using the image photographed by the photographing unit, detecting and displaying a first curve representing the actual moving distance of the blood cells in the centrifugal container every hour and a second curve representing a theoretical moving distance of the blood cells every hour, and measuring a degree of deformation of the blood cells by comparing the first curve and the second curve
    wherein the controller calculates the second curve using the following equation and measures the degree of deformation of the blood cells by using at least one of a height difference between the first curve and the second curve and a slope difference between the first curve and the second curve:

$$\frac{\pi}{6} p_p d_p^3 r_p'' = \frac{\pi}{6}(p_p - p_f)d_p^3 w^2 r_p - 3\pi d_p r_p' \left\{ u_f (1 + \theta^{1/3}) \exp\left[\frac{5\theta}{3(1-\theta)}\right] \right\}$$

in the equation, $\pi$ is a circle constant, $p_p$ is the density of the blood, $d_p$ is a diameter of the blood cells, $r''_p$ is a moving acceleration of the blood cells, $p_f$ is the density of the plasma, w is an angular velocity of the disk, $r_p$ is a moving distance of the blood cells, $r'_p$ is a moving speed of the blood cells, $u_f$ is the viscosity of the plasma and $\theta$ is a volume ratio of the blood cells to the entire volume of the blood.

2. The disk-shaped microfluidic system of claim 1, wherein the disk further comprises:
   a plasma container connected with the centrifugal container; and
   a micro-valve connected between the centrifugal container and the plasma container.

* * * * *